United States Patent [19]

Moshofsky

[11] 4,272,002
[45] Jun. 9, 1981

[54] INTERNAL SURGICAL STAPLER

[75] Inventor: Jerome F. Moshofsky, Portland, Oreg.

[73] Assignees: Lawrence M. Smith; G. Marts Acker; Franklin G. Smith, ; part interest to each

[21] Appl. No.: 59,667

[22] Filed: Jul. 23, 1979

[51] Int. Cl.³ .............................................. B25C 1/00
[52] U.S. Cl. .................................... 227/19; 227/135; 227/DIG. 1
[58] Field of Search ................. 227/19, 134, 135, 152, 227/DIG. 1, DIG. 2, DIG. 3, DIG. 4; 72/410

[56] References Cited

U.S. PATENT DOCUMENTS

| | | | |
|---|---|---|---|
| 3,079,606 | 3/1963 | Bobrov et al. | 227/DIG. 1 |
| 3,307,389 | 3/1967 | Rose et al. | 72/410 |
| 3,482,428 | 12/1969 | Kapitanov et al. | 227/DIG. 1 |
| 3,494,533 | 2/1970 | Green et al. | 227/DIG. 1 |
| 3,499,591 | 3/1970 | Green | 227/DIG. 1 |
| 3,646,801 | 3/1972 | Caroli | 227/DIG. 1 |

Primary Examiner—Paul A. Bell
Attorney, Agent, or Firm—Klarquist, Sparkman, Campbell, Leigh, Whinston & Dellett

[57] ABSTRACT

The specification discloses an improved multiple suture stapler in which two rows of staples are pushed by a comb-like ram out of a magazine of a frame and are clinched by an anvil releasably latched to the frame. The frame is of one-piece plastic construction and includes a pair of handles hinged to the magazine and having forwardly projecting, hinged arms welded to a push rod connected to the ram. One of the handles has a thumb grip used when the anvil is closed on the magazine. A stapler forming an alternate embodiment of the invention includes a latching rod splined to a frame with a thumb grip serving to push the latching rod into a latch mechanism of an anvil, and also adapted to be manually turned to turn the rod to a latch releasing position.

18 Claims, 14 Drawing Figures

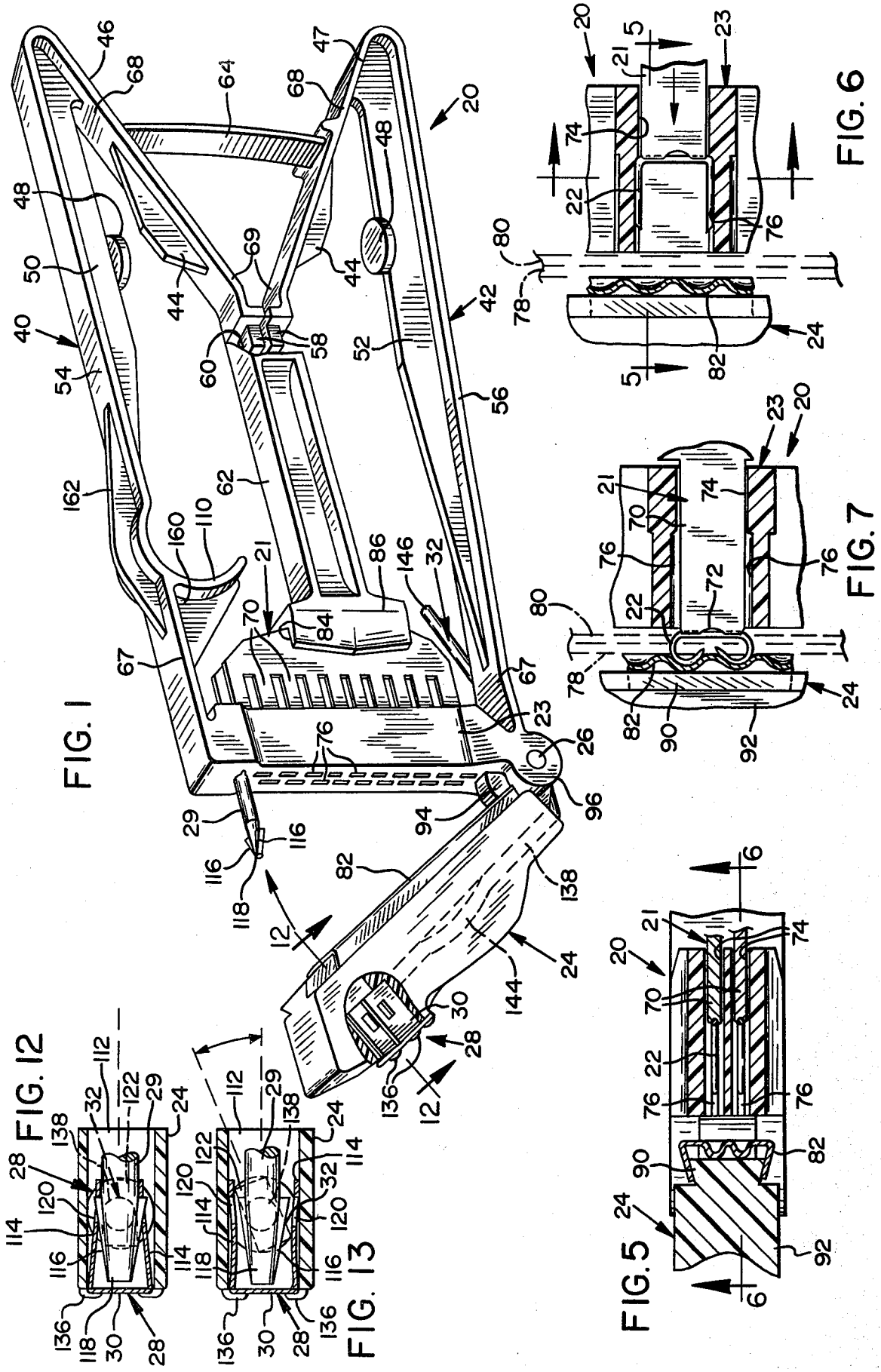

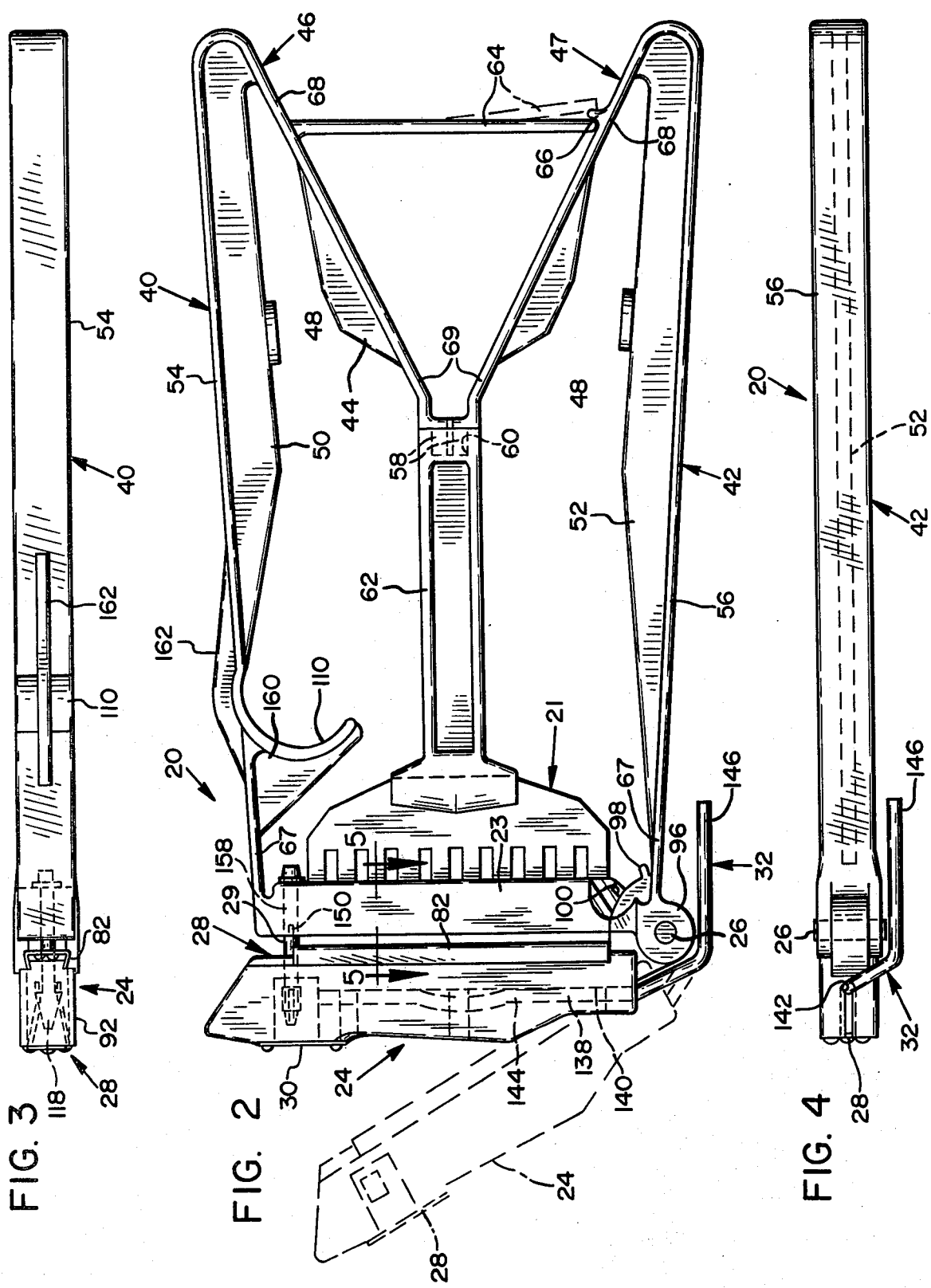

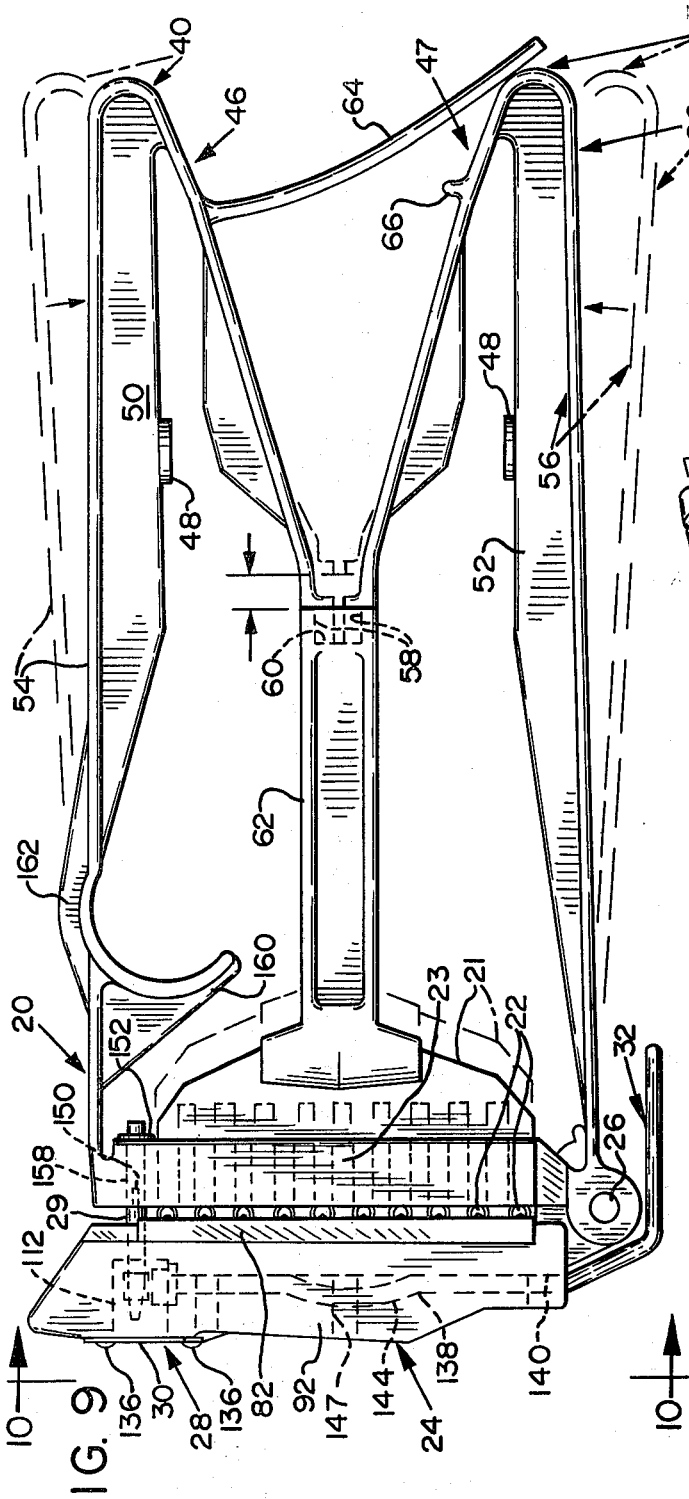
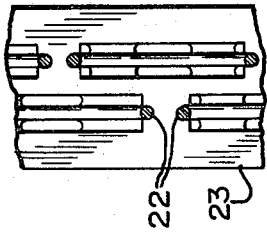
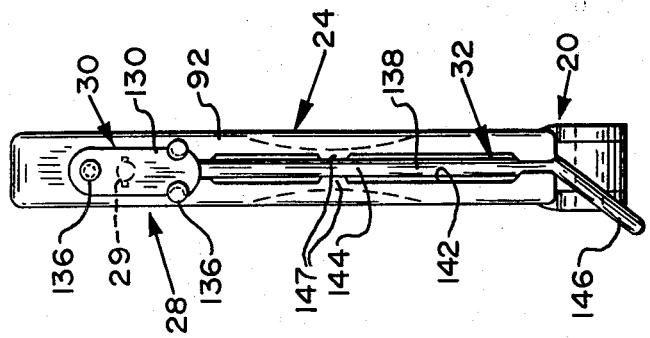
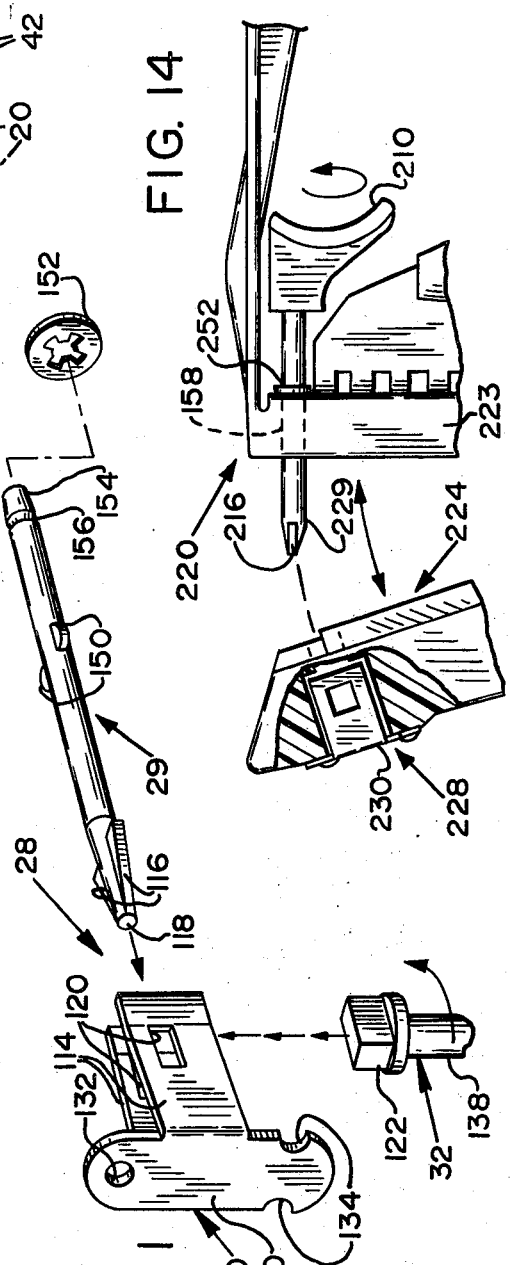

INTERNAL SURGICAL STAPLER

DESCRIPTION

This invention relates to improved multiple suture staplers, and has for an object thereof the provision of improved multiple suture staplers.

Another object of the invention is to provide a throwaway multiple suture stapler.

A further object of the invention is to provide a multiple suture stapler which is compact and easily manipulated.

Another object of the invention is to provide a multiple suture stapler having a pair of handles hinged to a magazine and adapted when passed toward each other, to push a ram through the magazine by means of arms hinged to the handles.

Another object of the invention is to provide a multiple suture stapler having a very compact manual driving mechanism capable of delivering a high stapling force.

Another object of the invention is to provide a multiple suture stapler having a one-piece molded plastic frame and driving mechanism.

Another object of the invention is to provide a multiple suture stapler including a magazine and a pair of handles hinged to the magazine and having arms connected to a push rod.

Another object of the invention is to provide a multiple suture stapler having a handle with a thumb grip for closing a magazine and an anvil.

Another object of the invention is to provide a multiple suture stapler having a spring latch carved by an anvil for engaging a latching rod on a frame, and a manually operable lever for releasing the latch.

Another object of the invention is to provide a multiple suture stapler having a piercing pin.

Another object of the invention is to provide a multiple suture stapler having a piercing pin carried by a frame, the pin having latching portions adapted to engage a latch member on an anvil to hold the frame and the anvil in clamping positions.

Another object of the invention is to provide a multiple suture stapler having a thumb grip secured to a latching rod on a frame and adapted to turn the rod to a releasing position relative to a latching member on an anvil.

BRIEF DESCRIPTION OF THE DRAWINGS

In the drawings:

FIG. 1 is a perspective view of an improved multiple suture stapler forming one embodiment of the invention;

FIG. 2 is a side elevation of the stapler of FIG. 1;

FIG. 3 is a top plan view of the stapler of FIG. 1;

FIG. 4 is a bottom plan view of the stapler of FIG. 1;

FIG. 5 is an enlarged, horizontal sectional view taken along line 5—5 of FIG. 2;

FIG. 6 is an enlarged, vertical sectional view taken along line 6—6 of FIG. 5 prior to a stapling operation of the stapler;

FIG. 7 is a view like FIG. 6 but with a staple driven and clinched;

FIG. 8 is an enlarged vertical sectional view taken along line 8—8 of FIG. 6;

FIG. 9 is a side elevation view of the stapler of FIG. 1 at the end of a staple-driving operation;

FIG. 10 is a front elevation view taken along line 10—10 of FIG. 9;

FIG. 11 is an enlarged, exploded perspective view of a latch of the stapler of FIG. 1;

FIG. 12 is an enlarged sectional view taken along line 12—12 of FIG. 1;

FIG. 13 is a view like FIG. 12 but with components of a latch shown therein in releasing positions;

FIG. 14 is a fragmentary perspective view of a multiple suture stapler forming an alternate embodiment of the invention.

EMBODIMENT OF FIGS. 1–13

Referring now in detail to the drawings, there is shown therein a multiple suture stapler forming a specific embodiment of the invention including a frame 20 adapted to drive comb-like rams 21 to move a multitude of suture staples 22 out of a magazine portion 23 thereof, through parts (not shown) to be sutured against an anvil 24 to clinch the staples. The anvil is hinged to the handle by a pin 26, and is movable between an open position as shown in FIG. 1 to a closed position as shown in FIG. 9 in which it is automatically latched by a latch 28 having a pin 29 and a spring member 30. A release lever 32 is operable manually to release the latch when desired.

The frame 20 (FIGS. 1, 2 and 9) is of a one-piece, molded plastic construction, the material preferably being of an acetal such as "Delsin" or an acrylic, and includes a driving mechanism comprising a pair of driving members 40 and 42 adapted to be gripped in one hand and, in stapling, moved toward each other from their normal or retracted positions shown in broken lines in FIG. 9 to their operated positions shown in full lines in FIG. 9, in the latter positions of which reinforcing ribs 44 of thrust arms 46 and 47 engage stops 48 on reinforcing ribs 50 and 52 of handle members 54 and 56.

The arms 46 and 47 have tangs 58 fitting in a socket 60 in a thrust rod 62 preferably also of the same material as the driving members 40 and 42 and suitably fastened, as by ultrasonically welding, to the arms 46 and 47 until ready for the stapling, a free end of a locking plate 64 integral with the arm 46 is in a flexed position extending into a notch formed by a stop 66 on the arm 47 and prevents closing movement of the arms. When ready for the stapling, the arms are spread apart and plate 64 springs out to its releasing position shown in broken lines in FIG. 2 and then does not prevent movement of the arms toward each other. Also, as an alternative way of release, the free end of the plate may be manually pushed sidewise into a position clearing the notch.

The driving mechanism, while easy to actuate, develops a very high force on the thrust rod, upward of fifty pounds as the staples are clinched. The members 54 and 56 have unribbed flexible hinge portions 67, and the arms 46 and 47 each has unribbed, flexible spring hinge portions 68 and 69. In effect then, the handle members 54 and 56 are rearwardly extending levers pivoted to the magazine portion 23, and the thrust arms 46 and 47 are forwardly and inwardly projecting levers pivoted to both the members 54 and 56 and the thrust rod 62 by the spring hinge portions 68 and 69, which normally hold the arms 46 and 47 the full-line positions thereof shown in FIG. 1, each arms 46 and 47 forming an angle of about thirty degrees with its handle member 56 or 57. This gives very high leverage which increases as the handle members are pressed toward each other in the stapling operation.

The two rams 21 (FIGS. 5, 6 and 7) are comb-like plates preferably of stainless steel and having tines 70 having grooved ends with arcuate central relief portions 72, the tines of one ram being staggered relative to the tangs of the other ram. The tines are slidable in guideways 74 to push the suture staples 22 out of grooves 76 in the magazine 23 through layers 78 and 80 to be sutured together and against anvil plate 82 of the anvil to clinch the staples as shown in FIG. 7. The staples are loaded into the slots 76 from their open ends and are held by friction in the slots until pushed by the anvils. The plate-like rams have arched backbone portions and fit tightly into a pair of parallel slots 84 (FIG. 7) in a head 86 of the push rod. When the closing grip on the handle members 40 and 42 is released, the rams are retracted by the handle members to their normal positions shown in FIG. 6.

The anvil plate 82 (FIGS. 1 and 5) preferably is of stainless steel, and is shaped to have a tight, dovetail fit on undercut rib 90 of anvil support 92 also preferably of a tough molded plastic material like that of the frame 20. The anvil support has a circular hinging portion 94 positioned in a clevis portion 96 of the frame and through which the pin 26 extends. A finger 98 on the hinging portion engages stop 100 to limit the normal or open position of the anvil relative to the frame as shown in FIG. 1.

To clamp the layer 78 and 80 together prepatory to stapling them together, the user places his thumb in an arcuate thumb grip 110 on the handle member 40 and his fingers around the anvil. He then presses the anvil and the frame 20 toward each other to drive the pin 29 through the layers 78 and 80, if necessary, and into a hole 112 in the anvil support and between spring arms 114 of the spring member 30 until ratchet teeth 116 of the tapered point portion 118 of the pin 29 come opposite to slots 120 in the arms 114, and the arms 114 spring back to the positions thereof shown in FIG. 12 to trap the pin. The latch holds the anvil 24 and the frame 20 in clamping positions while the stapling is effected after releasing the lock plate 64. Then to release the latch, the lever 32 is swung from its normal position shown in FIG. 12 to its releasing position shown in FIG. 13 in which a spreader or cam member 122 keyed to the lever 32 pushed the arms 114 apart to their release positions shown in FIG. 13, and the anvil is swung to its open position.

The spring member 30 has a base 130 (FIGS. 10 and 11) having a hole 132 and notches 134 through which headed plastic rivet members 136 extend to secure the member 30 to the anvil support 92. A shaft portion 138 of the lever 32 is rotatable in a bore 140 at the bottom of a slot 142 in the anvil support and narrower than the diameter bore. The shaft has an offset detenting portion 144 (FIG. 1) which normally is held by narrower lands 147 in a position holding the spreader 122 in its retracted position shown in FIG. 12 but permitting turning of the shaft portion by a handle portion 146 to its unlatching position shown in FIG. 13.

The pin 29 (FIG. 11), which is preferably of stainless steel, has keying tabs 150 driven into the frame 20 to keep the teeth 116 laterally aligned with the holes 120 (FIG. 12) in the arms 114. A spring washer 152 (FIG. 11) pushed over tapered end portion 154 and into groove 156 in the pin and the tabs hold the pin 29 against movement relative to the frame, the pin extending through bore 158 in the frame. The grip 110 (FIG. 1) is generally semi-cylindrical and a gusset 160 and a rib 162 rigidify that portion of the arm 40.

EMBODIMENT OF FIG. 14

An improved multiple suture stapler 220 forming an alternate embodiment of the invention is like the stapler 20 except that a latch 228 replaces the latch 28 and the release lever 29 and the thumb grip 110. The latch 228 includes a spring member 230 like the member 30. A latch pin 229 like the pin 29 except for the pin 229 being longer and having no keying tabs 150 and being rotatable in the bore 158. A thumb grip 210 keyed to the end portion of the pin 229 is engagable by the thumb to push the pin toward anvil 224 into latching engagement of the pin with the spring member 230, a spring washer 252 in a groove in the pin bearing against magazine 223 of frame 220. To release the latch the thumb grip is turned approximately 90° to turn teeth 216 of the pin out of latching engagement with the member 230. The pin 229 is suitably detented to normally hold the pin against turning.

What is claimed is:

1. In a suture stapler, holding means for holding a staple;
    ram means for pushing the staple out of the holding means; and
    a drive mechanism including a handle pivotally connected to the holding means and a thrust lever folded back on the handle and pivotally connected to the handle and the ram means so that, when the handle and the thrust lever are squeezed together, the ram means is moved through the holding means,
    the handle and the thrust lever being integral and including a spring hinge portion connecting them together.

2. The stapler of claim 1 including a thrust member connected to the ram means, the thrust member and the thrust lever being integral and including a spring hinge portion connecting them together.

3. The stapler of claim 1 wherein the handle and the holding means are integral and include a spring hinge portion connecting them together.

4. In a suture stapler, holding means for holding a staple;
    ram means for pushing the staple out of the holding means; and
    a drive mechanism including a handle pivotally connected to the holding means and a thrust lever folded back on the handle and pivotally connected to the handle and the ram means so that, when the handle and the thrust lever are squeezed together, the ram means is moved through the holding means,
    the holding means, the handle and the lever being integral, of molded plastic material, and including a first spring hinge portion connecting the handle to the holding means and a second spring hinge portion connecting the lever to the handle.

5. The stapler of claim 4 wherein the handle comprises a strip having a folded back portion at its free end and a stiffening rib integral with the strip, the first spring portion being the end portion of the strip connected to the holding means.

6. In a suture stapler, elongated holding means for holding a staple;
    ram means for pushing the staple out of the holding means;

a pair of handles pivotally connected to opposite ends of the holding means; and a pair of levers connected pivotally to the handles and the ram means and being in positions folded back relative to the handles, each handle being integral with one of the levers, the handles and the levers including spring hinge portions connecting them together.

7. The stapler of claim 6 including spring hinge means interconnecting the levers.

8. The suture stapler of claim 7 wherein the holding means, the handles and the levers are integral.

9. In a suture stapler, elongated holding means for holding a staple;

ram means for pushing the staple out of the holding means;

a pair of handles pivotally connected to opposite ends of the holding means; and a pair of levers connected pivotally to the handles and the ram means and being in positions folded back relative to the handles, the holding means comprising a magazine for holding a multitude of staples, the ram means including a multitude of pushers extending into the magazine for pushing the staples out.

10. The stapler of claim 9 including anvil means hinged to the magazine, latch means for holding the anvil means in a clamping position relative to the magazine, and means for releasing the latch means.

11. The stapler of claim 10 wherein the latch means includes a rod on the magazine and a leaf spring catch on the anvil means, the latch means being of the ratchet type adapted to latch when the anvil means is closed on the magazine.

12. The stapler of claim 10 or 11 including a thumb grip for pushing the magazine toward the anvil means.

13. The stapler of claim 12 wherein the thumb grip is mounted on one of the handles.

14. The stapler of claim 11 including a thumb grip mounted on the rod for pushing the rod and the magazine toward the anvil.

15. The stapler of claim 11 wherein the rod is rotatable relative to the magazine between a latching position and a releasing position, the rod having latch members on opposite sides only and the catch having a pair of arms having catch portions engagable by the latch members only when the rod is in its latching position.

16. The stapler of claim 10 wherein the anvil means includes an arm pivotal to the magazine and having a dovetail portion, the anvil means also including an anvil plate having clinching portions and being of dovetail shape and fitted interlockably on the arm.

17. In a multiple suture stapler, a magazine for holding staples;

an anvil hinged to the magazine for movement between a clamping position and a releasing position;

ram means;

drive means for moving the ram means to move the staples out of the magazine and clinchingly against the anvil;

a rod carried by the magazine and having a latching barb;

a leaf spring catch carried by the anvil and adapted to be engaged by the barb when the anvil is moved to its clamping position, said leaf spring catch comprising a pair of generally parallel spring arms adapted to be engaged by opposite sides of the barb; and release means for disengaging the barb and the catch, said release means comprising means for spreading said pair of spring arms apart.

18. In a multiple suture stapler, a magazine for holding staples;

an anvil hinged to the magazine for movement between a clamping position and a releasing position;

ram means;

drive means for moving the ram means to move the staples out of the magazine and clinchingly against the anvil;

a rod carried by the magazine and having a latching barb;

a leaf spring catch carried by the anvil and adapted to be engaged by the barb when the anvil is moved to its clamping position; and release means for disengaging the barb and the catch, the release means including means for rotating the rod to rotate the barb away from the catch.

* * * * *